United States Patent
Mecocci

(10) Patent No.: US 10,302,362 B2
(45) Date of Patent: May 28, 2019

(54) SENSOR-LESS ESTIMATION OF STEADY-STATE LOAD CONDITION

(71) Applicant: Eurotherm Limited, Shropshire (GB)

(72) Inventor: Francesco Mecocci, Worthing (GB)

(73) Assignee: Eurotherm Limited, Shropshire (GB)

( * ) Notice: Subject to any disclaimer, the term of this patent is extended or adjusted under 35 U.S.C. 154(b) by 112 days.

(21) Appl. No.: 15/380,444

(22) Filed: Dec. 15, 2016

(65) Prior Publication Data
US 2018/0172354 A1 Jun. 21, 2018

(51) Int. Cl.
*F27D 19/00* (2006.01)
*G01N 25/20* (2006.01)
*G05B 15/02* (2006.01)

(52) U.S. Cl.
CPC .............. *F27D 19/00* (2013.01); *G01N 25/20* (2013.01); *G05B 15/02* (2013.01); *F27D 2019/0028* (2013.01); *F27D 2019/0096* (2013.01)

(58) Field of Classification Search
CPC ............. F27D 19/00; F27D 2019/0028; F27D 2019/0096; G01N 25/20; G05B 15/02
See application file for complete search history.

(56) References Cited

U.S. PATENT DOCUMENTS

| | | | |
|---|---|---|---|
| 6,855,916 B1 * | 2/2005 | Matthews | F27B 17/0025 118/50.1 |
| 7,205,231 B2 * | 4/2007 | Frisella | H01L 21/67109 257/E21.082 |
| 7,404,670 B2 * | 7/2008 | Willis | F27B 14/00 219/483 |
| 8,729,158 B2 * | 5/2014 | Davis | B82Y 30/00 423/339 |
| 2004/0173142 A1 * | 9/2004 | Willis | F27B 14/00 117/200 |
| 2006/0094261 A1 * | 5/2006 | Frisella | H01L 21/67109 438/800 |
| 2011/0276169 A1 | 11/2011 | Bourg, Jr. et al. | |
| 2016/0146491 A1 * | 5/2016 | Ettl | G05B 15/02 700/276 |
| 2016/0146493 A1 * | 5/2016 | Ettl | G05B 15/02 700/29 |

FOREIGN PATENT DOCUMENTS

WO WO200180055 A2 10/2001
WO WO2004070339 A1 8/2004

OTHER PUBLICATIONS

Extended European Search report for application EP17205205.2 dated May 11, 2018, 5 pages.

* cited by examiner

*Primary Examiner* — Charles R Kasenge
(74) *Attorney, Agent, or Firm* — Stinson Leonard Street LLP

(57) ABSTRACT

Estimating the time of reaching steady-state uniform load temperature of a load in a heat treatment process in the absence of a load temperature sensor. In an embodiment, a system utilizes signals and parameters available on a temperature controller to estimate the period of time required for a load to reach a steady-state temperature in a heat treatment process. When the estimate of the temperature of the load reaches the steady-state condition, the system advances the heat treatment process from a load heating phase to another phase.

20 Claims, 13 Drawing Sheets

SENSOR-LESS ESTIMATION OF STEADY-STATE LOAD CONDITION

TECHNICAL FIELD

Aspects of the present disclosure generally relate to the field of heat treatment batch processes. More particularly, aspects of the present disclosure relate to the use of process controllers to control a furnace for the heat treating process of a thermal load in the absence of a load temperature sensor.

BACKGROUND

Heat treatment processes include loading a material, such as a metal, into a furnace and applying heat until the material (i.e., the load) reaches a steady-state temperature. The heat treatment itself starts typically when the material reaches uniform steady-state temperature within a certain tolerance defined by a specific temperature threshold: this condition of the load is defined as steady-state condition. If no treatment procedure is specified and there is no knowledge of the time required for the load to reach the steady-state condition, then conventional heat treatment processes utilize a load thermocouple inserted into the load to determine when the load reaches the steady-state temperature. However, utilizing load thermocouples has several disadvantages, including time delay due to the setup of the sensor and expense due to their replacement when the sensor wears. Knowledge of the time when the load has reached steady-state uniform temperature would allow advancement to the next step of the heat treatment process in the minimum time with consequent savings of time, energy, and costs and increase the throughput and the utilization of the furnace.

Without a load thermocouple and without a predefined procedure, conventional heat treatment processes rely on experience-based and/or indirect techniques of estimating the time required to heat the load to a target temperature. One such technique includes software models based on complex mathematics that rely on data such as emission constants, physical dimensions of the load, and how the load is placed in the furnace. This technique is unreliable when such parameters are not available and is not suitable for implementation on process controllers. Another technique includes a human operator opening the furnace to view the load. This technique requires highly experienced operators and also introduces a temperature loss. Yet another technique includes measuring the active electrical power supplied to the furnace and assessing when it has reached the steady-state condition. But the active power measurement is not always available and this property is indirect in relation to the load temperature. In fact, the power time profile is affected by changes to the size and shape of the load and therefore the relation between load temperature and supplied power is dependent on the particular load. These conventional techniques are unsuitable for implementing a sensor-less identification of the load steady-state condition that is robust against the variation of the load and at the same time a simplified and immediate interface through which the user can set the desired load temperature threshold to be achieved.

SUMMARY

Aspects of the disclosure include systems and methods for the automatic identification of the end of a load heating phase and the automatic advancement to a next step of a heat treatment process in the absence of a load temperature sensor by using the intersection of a real-time estimated load core temperature ($TL_{est}$) with the difference between a temperature setpoint (SP) and a user-entered load temperature threshold ($SS_{thr}$) as criterion to assess when the load has reached a steady-state condition. Further aspects of the disclosure include systems and methods for estimating the time of reaching steady-state uniform load temperature of a load in a heat treatment process in the absence of a load temperature sensor by using signals and parameters available on a temperature controller. Further aspects of the disclosure enable users to enter values into a controller that have immediate physical meaning, such as a desired load temperature threshold ($SS_{thr}$) and a time limit for the achievement of the load steady-state condition. Further aspects of the disclosure enable exposure of the load temperature estimation and signaling the end of the load heating phase to the user in a heat treatment process in the absence of a load temperature sensor. Furthermore, aspects of the present disclosure relate to methods to reduce energy consumption, increase the overall equipment effectiveness and simplify the user operations in heat treatment processes of thermal loads in the absence of a load temperature sensor.

In an aspect, a system includes a heat treatment furnace, a controller, and a human machine interface coupled to the controller. The controller is coupled to the furnace for controlling one or more operating parameters of the furnace. The controller includes a computer-readable storage device storing processor-executable instructions that, when executed, generate in real-time an estimate of a temperature of a load within the heat treatment furnace and perform a batch program that includes a load heating phase and at least one other phase. The controller receives a temperature setpoint and a load threshold via the human machine interface. The controller collects, during the load heating phase, samples of an available control loop signal when it is exponentially converging toward its steady-state value. The controller fits the collected samples with an exponential curve representing the slowest decay mode of the control loop signal. The controller generates a load temperature estimate by mapping the fitted exponential curve to the estimate of the temperature of the load. The controller advances the batch program from the load heating phase to the at least one other phase when the estimated load temperature reaches the difference between the temperature setpoint and the load threshold.

In another aspect, a controller executing computer-executable instructions monitors a setpoint ramp phase and a controller output saturation phase of a batch, during which heat is applied to a load within a heat treatment furnace. The controller collects samples of a control loop signal of the controller when the control loop signal is exponentially converging toward its steady-state value). The controller fits the collected samples with an exponential curve that is characterized by a time constant of a slowest exponential mode that is present in the control loop signal. The controller maps the fitted curve to estimate the temperature of the load. And the controller automatically advances to the next batch phase when it establishes that the estimated temperature of the load reaches the difference between a temperature setpoint and a load threshold.

In yet another aspect, a tuning procedure is embodied for the sensor-less load temperature estimation. A PID loop component of a controller is tuned against a heat treatment furnace in the absence of a load to generate a tuning set. The controller stores the tuning set in a computer-readable storage device. A load whose dynamics is dominant against the other system components, which includes a temperature sensor, is inserted into the heat treatment furnace. The controller receives a load threshold value of the temperature of the load from a setpoint temperature value and measures the temperature of the load while a heat source of the furnace is applied to the load. The controller collects samples a control loop signal when the control loop signal is exponentially converging toward its steady-state value and fits the collected samples with an exponential curve. The controller establishes the values of the mapping parameters from the sampled control loop signal and the estimated load temperature. The load is removed from the furnace and a sensor-less production load is inserted into the furnace. The controller estimates the temperature of the production load while the heat source of the furnace is applied to it based on the established values of the mapping parameters.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Aspects of the disclosure permit estimating the time of reaching steady-state uniform load temperature of a load in a heat treatment process in the absence of a load temperature sensor and advancing automatically to a next step of a heat treatment process by comparing the estimated temperature with the difference between a temperature setpoint and a user-entered load threshold. Further aspects of the disclosure enable users to enter values into a controller that have immediate physical meaning, such as a desired load temperature threshold ($SS_{thr}$) and a time limit for the achievement of the load steady-state condition. Further aspects of the disclosure display (e.g., through a human machine interface) the load temperature profile estimated in real-time by the controller. Further aspects of the disclosure notify users when the load heating phase has finished according to the estimation of a controller in the absence of a load temperature sensor.

Figure 1:
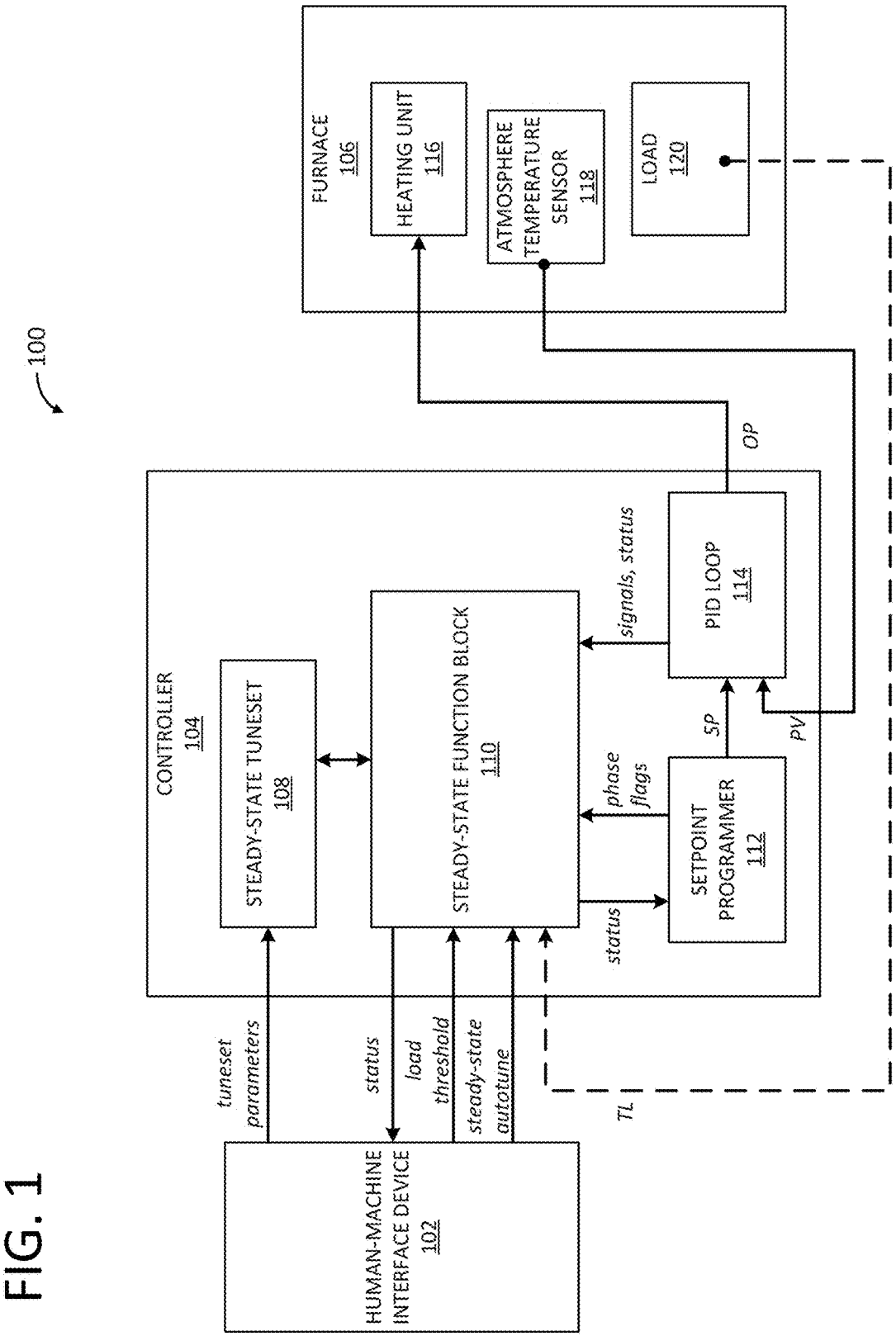
FIG. 1 is a block diagram illustrating an exemplary control system within which aspects of the disclosure may be incorporated.

FIG. 1 illustrates an exemplary control system, generally indicated at 100, within which an embodiment of the disclosure may be incorporated. The system 100 includes a user human-machine interface (HMI) device 102, a controller 104, and a furnace 106. The HMI device 102 may be embodied in the controller 104, in accordance with an aspect of the disclosure. The controller 104 includes a steady-state tuneset component 108, a steady-state function block 110, a setpoint programmer component 112, and a proportional-integral-derivative (PID) loop component 114. The furnace 106 includes a heating element 116 and an atmosphere temperature sensor 118. A load 120 may be located within the furnace 106. In an embodiment in which the system 100 performs a steady-state auto-tune process, as further described herein, the load 120 may include a temperature sensor inserted therein to sense the temperature of the load 120.

In accordance with an aspect of the present disclosure, a user enters a desired load threshold from a setpoint temperature that the load 120 must reach before the controller 104 will advance automatically to a next heat treatment phase (e.g., a load soaking phase). In an embodiment, a user may enter the minimum and maximum time limits for the activation of a steady-state status flag to manage undesired situations, such as underdamped and/or overdamped process variable responses (i.e., before the minimum time a steady-state status flag is held false and after the maximum time a steady-state status flag is forced to true). The controller 104 executing the algorithm utilizes the desired load temperature threshold to establish if the steady-state condition of the load temperature has been reached. The difference between the setpoint and the predicted load temperature is evaluated and if it is below the input load threshold the output steady-state indication flag is activated.

In accordance with another aspect of the present disclosure, controller 104 applies data filter techniques, curve fitting techniques, and properties of linear dynamical systems to solve the problem of the explicit prediction of load temperature in a batch heat treatment process that allows for detecting the end of a load heating phase and automatically advance to a next phase of the batch program. In an embodiment, controller 104 utilizes three main techniques combined together.

The first technique is data filtering against process disturbances and noise. In order to eliminate the effects of process disturbances and noise on the control loop signal used to map the load temperature (TL), a set of averaged samples are collected on a moving time window. Each sample is the mean of the real-time values acquired/calculated during the averaging/sampling period. The base sampling period is defined as a multiple (e.g., $1 \cdot T_i$) of a proportional-integral-derivative (PID) loop integral time constant ($T_i$, that is contained in the tuneset of the PID loop 114) and it self-adjusts depending on the duration of the load heating phase. When the maximum number of samples has been reached (e.g., ten samples) and a new sample has been calculated, the oldest sample is discarded and the last new sample is included in the set of samples (i.e., the collection of samples is implemented as a first-in first-out queue in accordance with an embodiment of the disclosure).

The second technique is curve fitting for the identification of the slowest mode of the closed-loop system. The controller 104 executing the algorithm identifies the time when the dynamics of the closed loop system is governed only by the effect of the load heating. From that time onwards the convergence rate of all the signals, towards their own steady-state value, is the same. The slowest converging mode is iteratively identified by applying a least square error method to the moving window samples of the control loop signal used to map the load temperature TL. The continuous adaptation to the current control loop signal shape allows for eliminating the residual effect of the high frequency transient closed loop dynamics not related to the load heating.

The third technique is utilizing linear dynamical system properties to estimate load temperature. When the dynamics of the closed loop system is governed only by the effect of the load heating, the control loop signals can be approximated with the slowest exponential decay mode plus the respective convergence value. After identifying the slowest exponential decay mode of the selected control loop signal, its current value and its parameters are used to estimate the actual load temperature (TL) by mapping the control loop signal mode to the actual load temperature TL mode that in turn approximate TL itself. The explicit prediction of TL is used to estimate the difference between the load temperature and SP. Based on the estimated difference, controller 104 determines when the load temperature reaches the steady-state condition and therefore the end of the load warming phase.

In accordance with yet another aspect of the present disclosure, controller 104 performing the described processes embeds a tuning functionality which may be used to setup the estimation algorithm for TL. In an embodiment, the tuning procedure is performed once on the same furnace/oven 106 by equipping with a temperature sensor a load 120 whose dynamics are dominant against the other system components. During the tuning procedure a normal heat treatment sequence is performed and the user is expected to enter a desired load temperature threshold for the load, and the actual load temperature is required in order to assess when the steady-state condition is reached and setup accordingly the estimation algorithm. In other words, the tuning procedure is aimed to setup the explicit load temperature estimation algorithm, rather than finding a threshold of other signals (e.g., controller output (OP), furnace atmosphere temperature (PV), supplied power) corresponding to the load steady-state condition. In the tuning procedure the actual TL is available and the actual difference between TL and SP is evaluated. A normal batch procedure is performed and when the actual steady-state condition is reached (defined by the desired load threshold entered by the user), the functionality sets automatically the internal prediction algorithm and it is ready to predict the steady-state condition for different loads. The parameters internally calculated/stored are the target SP used and the initial condition of the slowest TL mode.

Referring further to FIG. 1, in an embodiment, the controller 104 comprises a computing device programmed to provide aspects of the present disclosure via a software environment. In this embodiment, controller 104 includes a processor and a computer-readable storage device for storing computer-executable instructions (e.g., a memory). The computer-readable storage device includes steady-state tuneset component 108, steady-state function block 110, setpoint programmer component 112, and PID loop component 114 each embodied in processor-executable instructions for executing by the processor. In this manner, controller 104 comprises a special-purpose computing device for estimating the amount of time required for load 120 to reach a steady-state uniform load temperature in the absence of a load temperature sensor and automatically advancing to a next phase of the heat treatment procedure.

Figure 2:
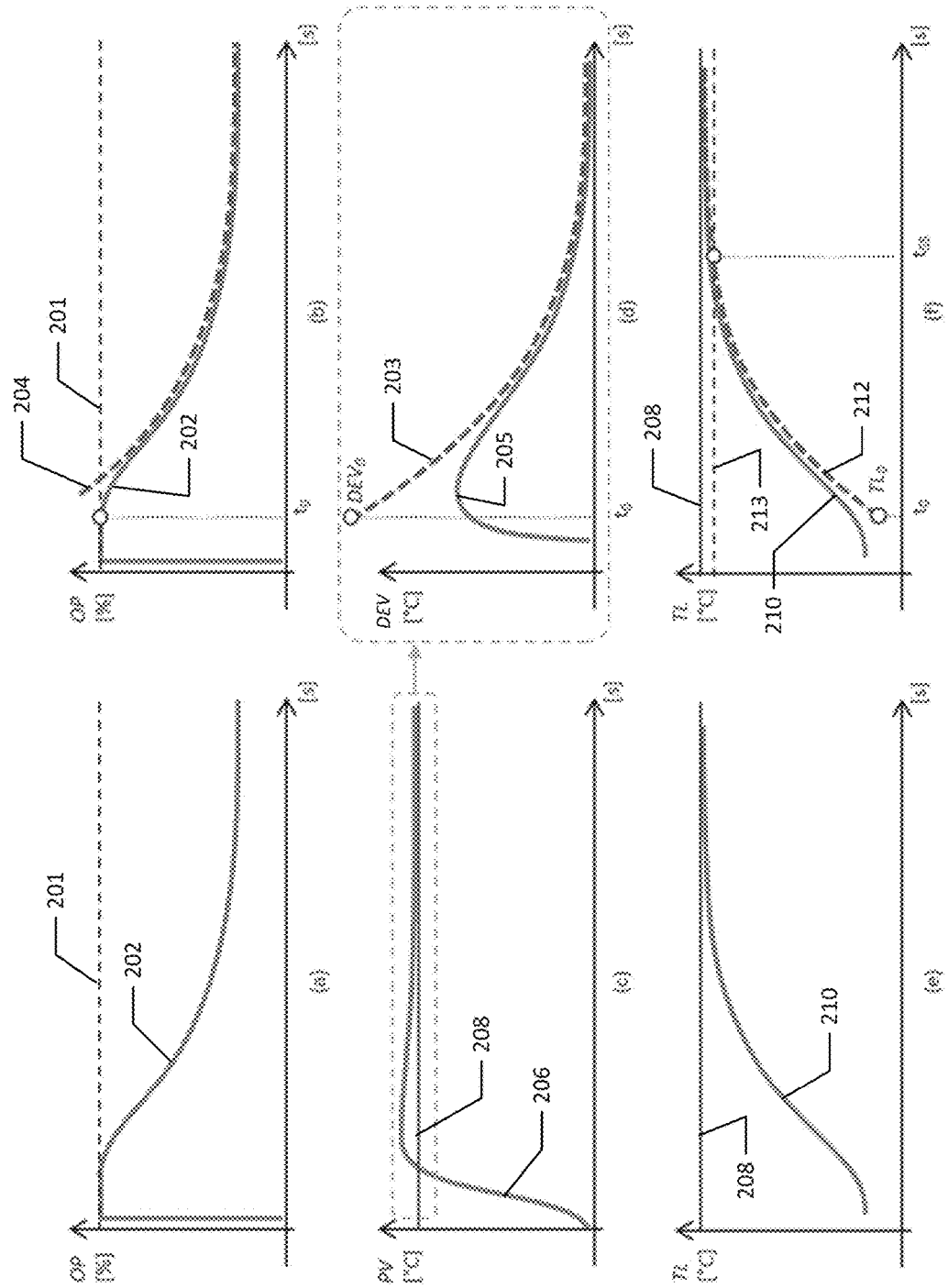
FIG. 2 illustrates exemplary value profiles representative of principles behind a steady-state execution process according to an embodiment.

FIG. 2 illustrates value profiles representative of principles behind an exemplary steady-state execution process performed by system 100. Plots (a)-(f) represent values of percentage controller output (OP), temperature of the controlled zone (PV), and load temperature (TL) during a load heating phase of a heat treatment batch. Plot (a) includes a profile 202 representing the OP value and a profile 201 representing the OP maximum value, over time (e.g., denominated in seconds (s) in the illustrated embodiment). In an embodiment, the OP value is the output of controller 104 that drives the power delivered to furnace 106. Plot (b) includes the profiles 201, 202 and a profile 204 representing a fitting OP decay mode curve over time. Plot (b) also includes an initial time ($t_O$), which defines the moment when the OP leaves the saturation. Plot (c) includes a profile 206 representing the PV value, which is the controlled process variable (e.g., atmospheric temperature in furnace 106). Plot (c) also includes a temperature setpoint (SP) 208. Plot (d) includes portions of the profiles 206 and 208 combined together to obtain the process deviation DEV=PV−SP, illustrated as profile 205, and also includes a profile 203 representing a fitting DEV decay mode curve over time. Plot (d) differs from Plot (c) in that the x-axis is shifted up by SP (DEV=PV−SP). Plot (e) includes a profile 210 representing the TL value, which is the temperature of load 120, over time. Plot (e) also includes the SP 208. Plot (f) includes the SP 208 and the profile 210 in addition to a profile 212 representing the TL value estimated by controller 104 and a profile 213 representing the difference between the temperature setpoint and the steady-state temperature threshold (e.g., SP−$SS_{thr}$) of the load. Plot (f) also includes the time ($t_{SS}$) when the load steady-state condition is estimated to be met. An algorithm in accordance with an aspect of the disclosure identifies the process deviation DEV slowest exponential decay mode 203, maps 203 to the TL slowest exponential decay mode 212, uses that as estimation of the load temperature (TL) 210 and estimates the end of the load warming up phase at time $t_{SS}$ when the estimated load temperature 212 reaches the difference between the temperature setpoint and the threshold temperature level 213.

In an embodiment, a principle of the steady-state execution process is that the effect of heating load 120 is present in control loop signals (e.g., the process variable PV, the controller output OP, the process deviation DEV=PV−SP). When furnace 106 heat treats a load 120, the steady-state value of the percentage controller output (OP) compensates the heat losses of the furnace. When load 120 uniformly reaches the setpoint temperature (SP), it no longer absorbs power. In a load heating phase of the process, load 120 absorbs power and the absorbed power decreases as the load temperature increases. The principle is illustrated by Plots (b) and (f) of FIG. 2, in which OP decreases over the time period and TL increases over the same time period. The decrease of OP is due to the decrease of the deviation between PV and SP (e.g., PV−SP). Plot (d) of FIG. 2 illustrates how the slowest decay modes due to load 120 present in the control loop signals PV and OP are characterized by the same decaying rate of the slowest decay mode of TL.

In an embodiment, a principle of the steady-state execution process is the mapping of a control loop signal to the estimated load temperature 212 when the control loop signal can be approximated with the slowest decay mode, due to the effect of the load 120, plus its convergence value. The asymptotic convergence value is used to map the control signal to the estimated load temperature 212. Therefore, using one of the signals that have a known convergence value introduces the advantage of knowing an element of the mapping equation from the selected control loop signal to the estimated load temperature 212 (e.g., PV and DEV that respectively converge to SP and 0 because of the control action of the PID loop 114). Using instead a signal that converges to an unknown value would require the identification of its convergence value in order to map the signal to the estimated load temperature 212. For instance, a controller output OP converges to the value associated with the power losses, which depends on the furnace insulation characteristics and on the ambient temperature. The real-time identification of the OP steady-state value would require adding complexity to the steady-state execution process due to an additional identification mechanism. Otherwise, the off-line identification of the OP steady-state value would require adding a specific experiment (e.g., at empty furnace) and assuming that the furnace maintains its properties over the time and that the ambient temperature effect can be neglected.

In an embodiment, controller 104 uses the shape of the process deviation (DEV=PV−SP) to estimate TL. The controller 104 identifies the slowest exponential decay mode on DEV and its time constant τ. The time $t_0$ is automatically identified as the moment when OP leaves the saturation. The formal expression of the fitted DEV curve is used to derive the value $DEV_0$, which is the value of the DEV mode at time $t_0$. The controller 104 back-calculates the value of the DEV mode at time $t_0$ by using the fitted exponential curve expression. This value can change while the sampling window moves and the fitting curve adapts to the DEV shape. The controller 104 then maps the DEV curve into the estimated TL, using SP, $DEV_0$, and $TL_0$ as parameters. The value $TL_0$ is the value of the TL mode at time $t_0$. In an embodiment, controller 104 calculates the value of the TL mode at time $t_0$ by using the previously evaluated ramp and saturation periods $t_R$ and $t_S$, the slowest mode time constant τ, and the tuning parameter $TL_{tun}$. $TL_{tun}$ represents the value of the TL mode at the beginning of the ramp phase (i.e., at the beginning of the heat treatment process) and it may be identified by an auto-tune process, as further described herein, or left to its default value (e.g., $TL_{tun}$=0). In an embodiment, the default value is dependent upon the type of furnace and/or operating conditions. The controller 104 estimates TL by using $TL_0$, $DEV_0$, and a mapping equation (e.g., Equation (1)). A steady-state output flag is switched on when the estimated load temperature ($TL_{est}$) reaches the difference between the temperature setpoint and the user-entered load threshold (e.g., SP−$SS_{thr}$).

$$TL_{est} = \frac{TL_o - SP}{DEV_0} DEV + SP \quad (1)$$

The principles illustrated by FIG. 2 assume that the load temperature heating time period is significantly longer than the furnace atmosphere heating time period (i.e., load dynamics are dominant), the temperature is uniform in the furnace, the load temperature can reach the SP value, and tuning of PID loop component 114 is tuned against an empty furnace 106 (i.e., without load 120). But the assumption that the temperature is uniform in the furnace is not essential for operation of the algorithm described herein. In an embodiment in which the temperature is not uniform in the furnace, the temperature of the load does not reach the setpoint but the steady-state temperature of the load is less than the setpoint (e.g., $TL_{ss}$<SP). The controller 104 estimates the time when the load reaches uniform temperature within the normalized threshold, $SS_{thr} \cdot TL_{ss}$/SP. In an embodiment, controller 104 executing the algorithm estimates the load uniformity in percentage terms, scaling the absolute threshold $SS_{thr}$ to $TL_{ss}$.

Figure 3:
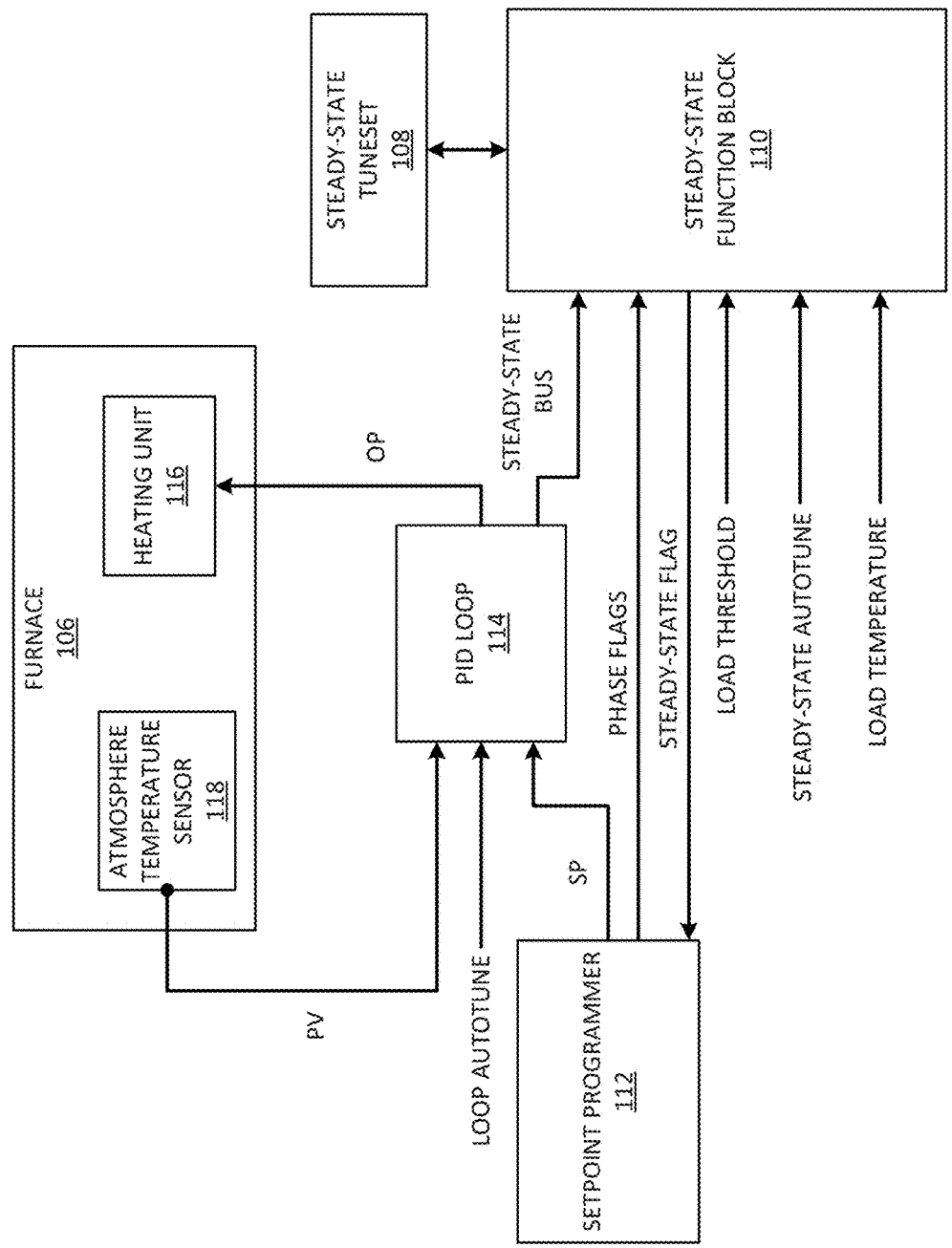
FIGS. 3-5B illustrate the control system of FIG. 1 during an exemplary user workflow according to an embodiment.

FIGS. 3-5 illustrate system 100 during an exemplary user workflow for initializing and utilizing the temperature estimation process in accordance with an aspect of the disclosure. FIG. 3 illustrates system 100 during a loop auto-tune phase of the user workflow in which PID loop component 114 is tuned against the empty furnace 106. In an embodiment, this step of the user workflow is skipped by assuming that the PID loop 114 has been previously tuned against the furnace 106 in empty condition (i.e., without any load), as further described herein. As illustrated, inputs to steady-state function block component 110 include the target temperature deviation between the load and the target setpoint temperature SP, the maximum and minimum time for steady-state identification, tuning activation, and load temperature when in the tuning mode. Inputs from PID loop 114 and a programmer include PV, OP, SP, tuning constants, and phase indication flags (e.g., SP ramp, OP saturation, load heating). Inputs from PID loop 114 may be all included in a steady-state bus signal. In an embodiment, a user starts the autotune of PID loop 114 with empty furnace 106. The result of the loop auto-tune phase is that PID loop component 114 will calculate the tuning set considering the atmosphere dynamics of furnace 106 in the absence of load 120. The PID loop component 114 passes the calculated tuning set through a steady-state bus to steady-state function block 110 where it is stored in a non-volatile memory structure comprising steady-state tuneset component 108.

Figure 4A:
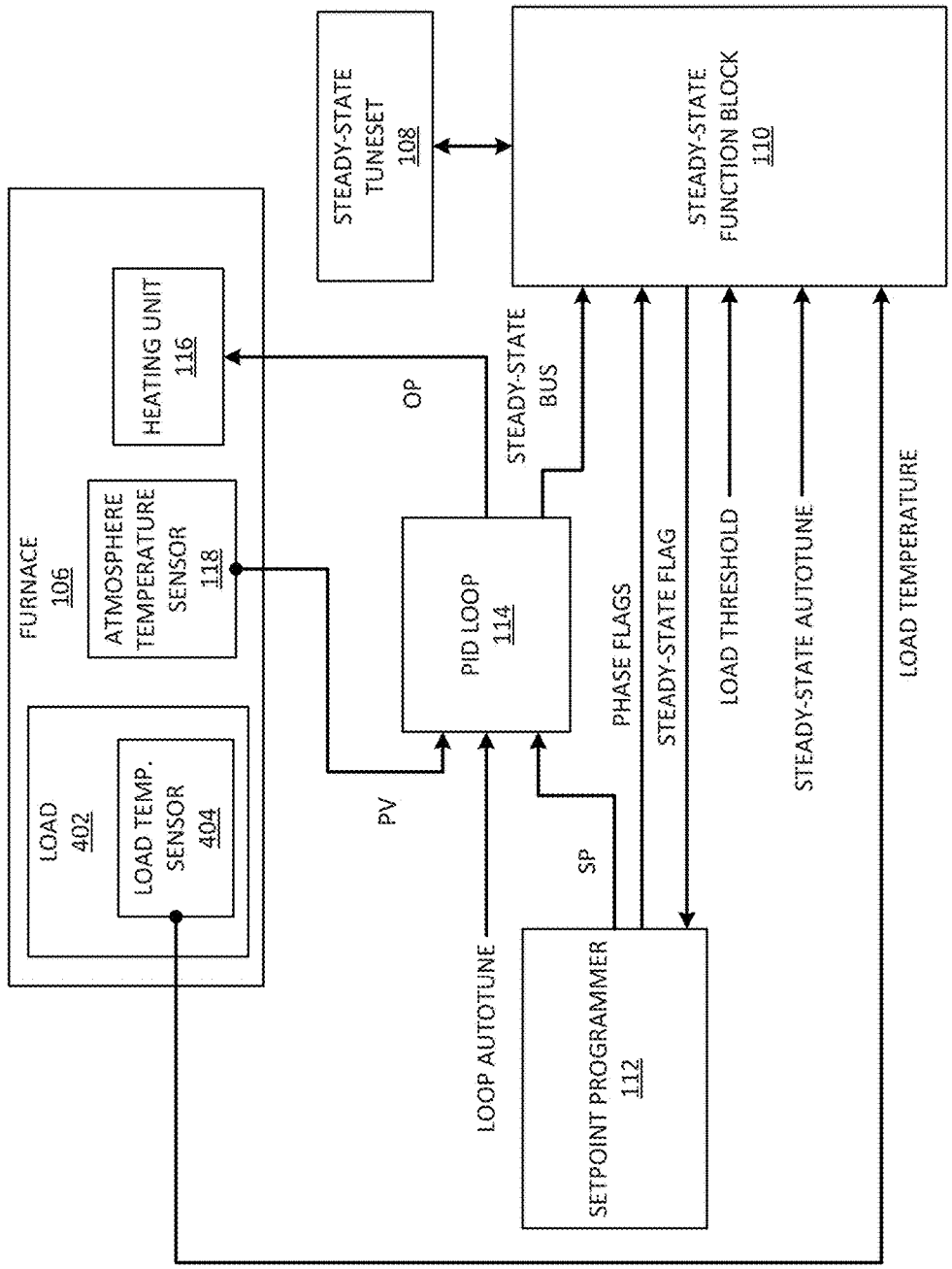
Figure 4B:
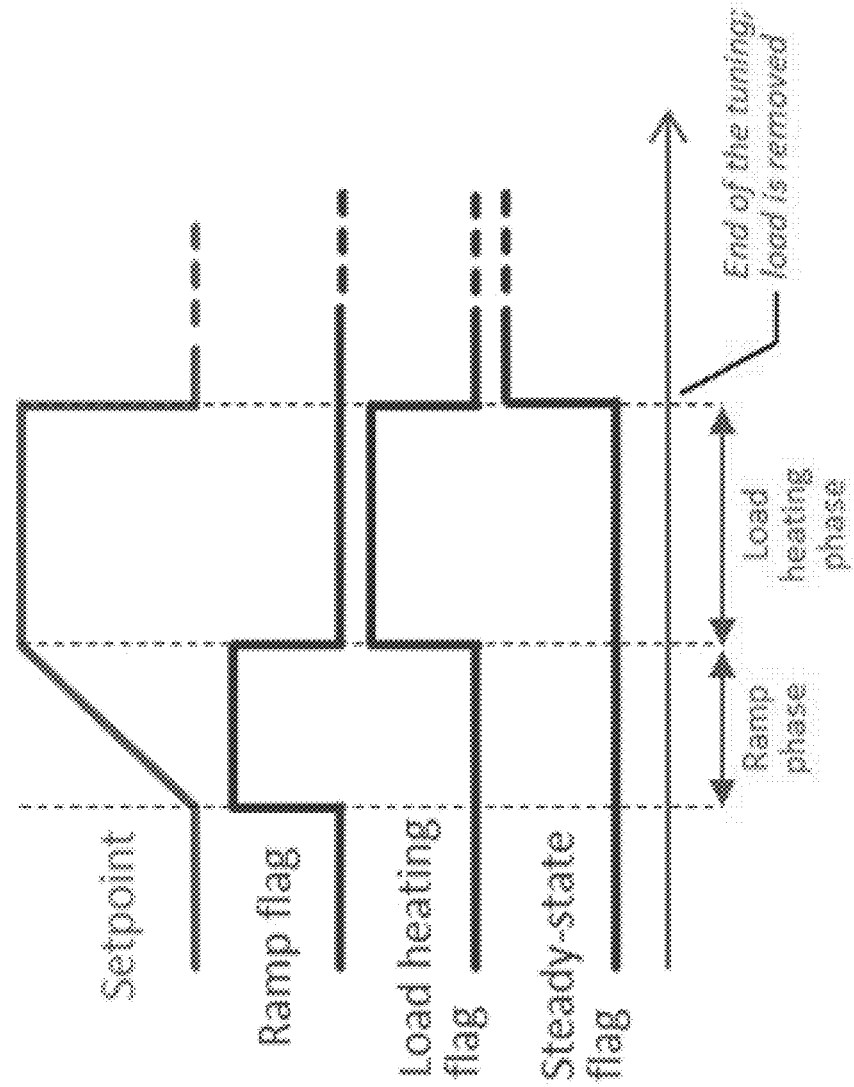

FIG. 4A illustrates system 100 during a steady-state auto-tune phase of the user workflow in which controller 104 tunes the steady-state algorithm against furnace 106 and a load 402 whose dynamics is dominant against the other system components. In an embodiment, this step of the user workflow is skipped and the steady-state function block component 110 will use the default value of the steady-state tuneset 108 (e.g., $TL_{tun}$=0). The load 402 is equipped with a load temperature sensor 404 (e.g., a thermocouple). The output of load temperature sensor 404 is transmitted to steady-state function block component 110. In an embodiment, a user enters a load threshold of the load temperature from the temperature setpoint, SP and starts the auto-tune of steady-state function block 110. The controller 104 utilizes the load threshold to evaluate the actual steady-state condition relative to the actual load temperature. In an embodiment, a setpoint program of setpoint programmer component 112 is configured with a batch program comprising, as illustrated by FIG. 4B, a SP ramp phase and a load heating phase. The steady-state function block component 110 assesses the start, the end, and the duration of the SP ramp phase and of the OP saturation phase (e.g., by using status indication flags from the setpoint programmer 112 and the PID loop 114). In an embodiment in which no SP ramp is used the ramp phase is not present and only the load heating phase is present. The steady-state auto-tune phase finishes when the load 402 reaches the steady-state condition. The steady-state function block component 110 saves, in the steady-state tuneset component 108, the parameters used to map DEV=PV−SP into TL in such a way that the mapped load temperature $TL_{est}$ reaches the steady-state condition at the same time of the actual load temperature TL. In other words, the steady-state function block component 110 stores the initial condition $TL_{tun}$ of the TL slowest mode and the SP used during the tuning in steady-state tuneset 108, which is used to calculate the scale factors of the mapping equation from DEV=PV−SP to $TL_{est}$ such that $TL_{est}$ and TL coincide at the achievement of the steady-state load condition (e.g., $TL=SP-SS_{thr}$).

In the steady-state auto-tune procedure, the process deviation profile DEV=PV−SP is fitted with the exponential curve (e.g., similar to the normal operation mode). The exact steady-state time ($t_{SS}$) is evaluated by the steady-state function block 110, which is the time when the actual load temperature reaches the difference between the temperature setpoint and the user-entered load threshold (e.g., $SP-SS_{thr}$). The actual measurement of the load temperature is therefore required during the steady-state auto-tune procedure. If the target setpoint temperature SP was not subject to ramp and the OP has not saturated to its maximum level, then the effects of SP ramp and OP saturation are null and $TL_{tun}=TL_0$ and its value can be derived by inverting the flipping equation, as described by Equation (2).

$$SP - SS_{thr} = \frac{TL_{tun} - SP}{DEV_0} DEV_{fit}(t_{ss}) + SP \quad (2)$$

where $$DEV_{fit}(t_{ss}) = \delta \exp(-t_{ss}/\tau) \quad (3)$$

is the exponential curve fitted on the PV samples evaluated at $t_{SS}$. Therefore the auto-tuned $TL_{tun}$ can be derived:

$$TL_{tun} = SP - \frac{1}{1-\lambda} SS_{thr} \quad (4)$$

where $$\lambda = \frac{DEV_0 - DEV_{fit}(t_{ss})}{DEV_0} \quad (5)$$

The correction of $TL_{tun}$ depending on ramp and saturation effect is further described herein.

Figure 5A:
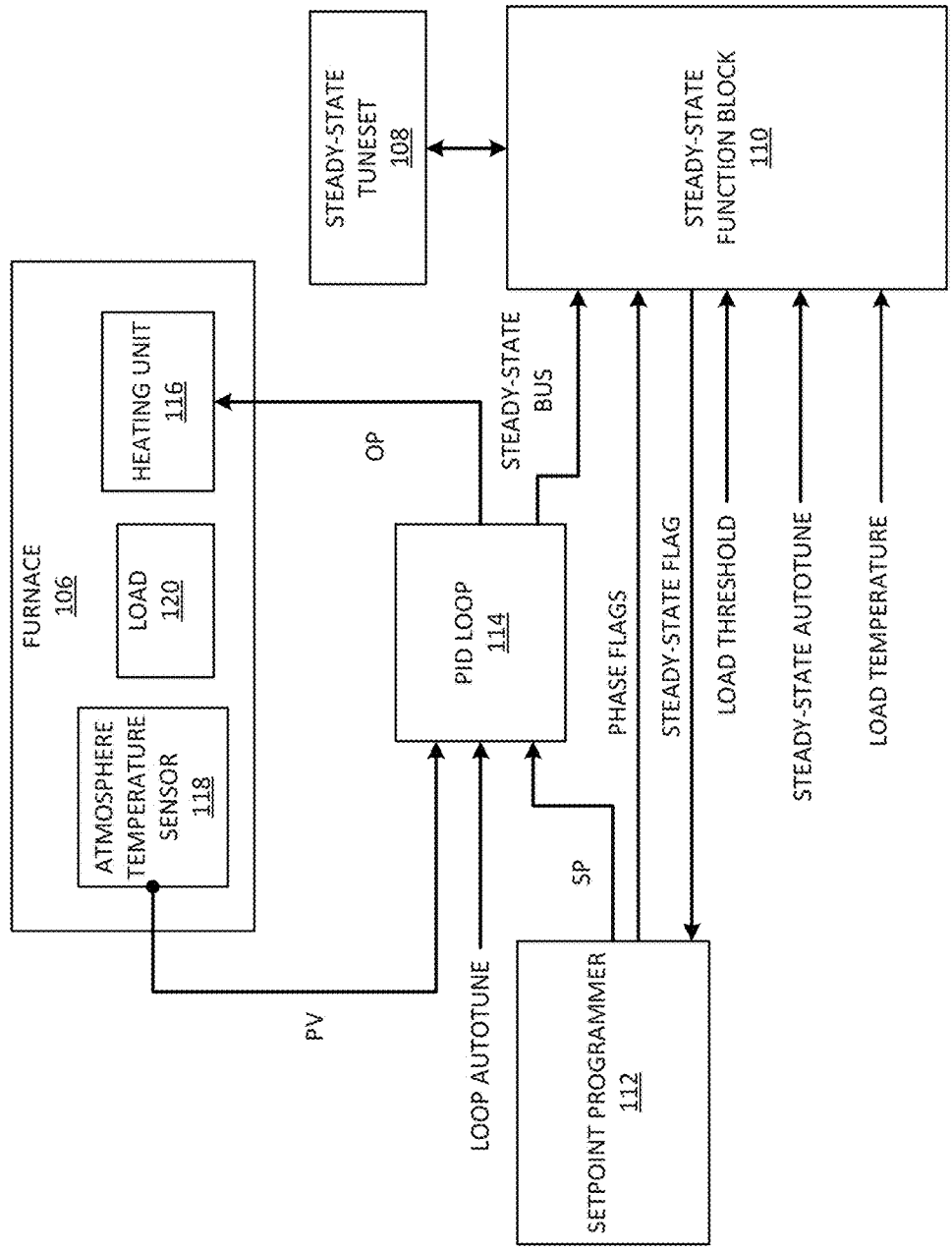
Figure 5B:
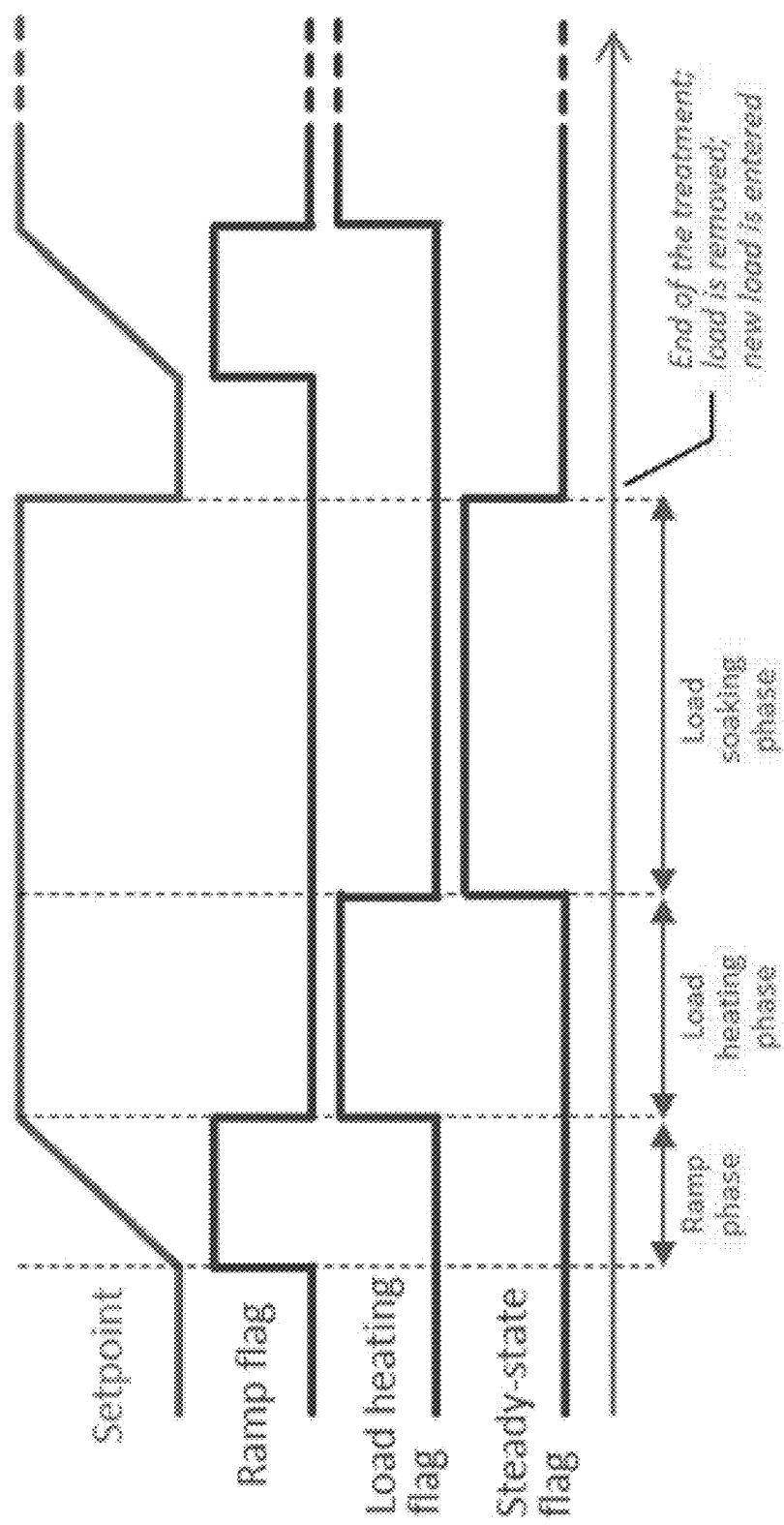

FIG. 5A illustrates system 100 during a steady-state execution phase of the user workflow. In an embodiment, load 120, without a load temperature sensor, is placed into furnace 106. A setpoint program of setpoint programmer component 112 is configured with a batch program comprising, as illustrated by FIG. 5B, a SP ramp phase and a load heating phase. The steady-state function block component 110 estimates the amount of time required for load 120 to reach a steady-state uniform load temperature in the absence of a load temperature sensor and with respect to the user-entered load threshold from the target setpoint temperature SP. The steady-state function block component 110 switches on a steady-state output indication flag when it has assessed that the load 120 has reached the steady-state condition. The setpoint programmer 112 receives as an input the steady-state status flag from the steady-state function block component 110. The setpoint programmer 112 advances automatically to the next phase of the heat treatment process (e.g., a load soaking phase) when the steady-state status flag is switched on.

Figure 6:
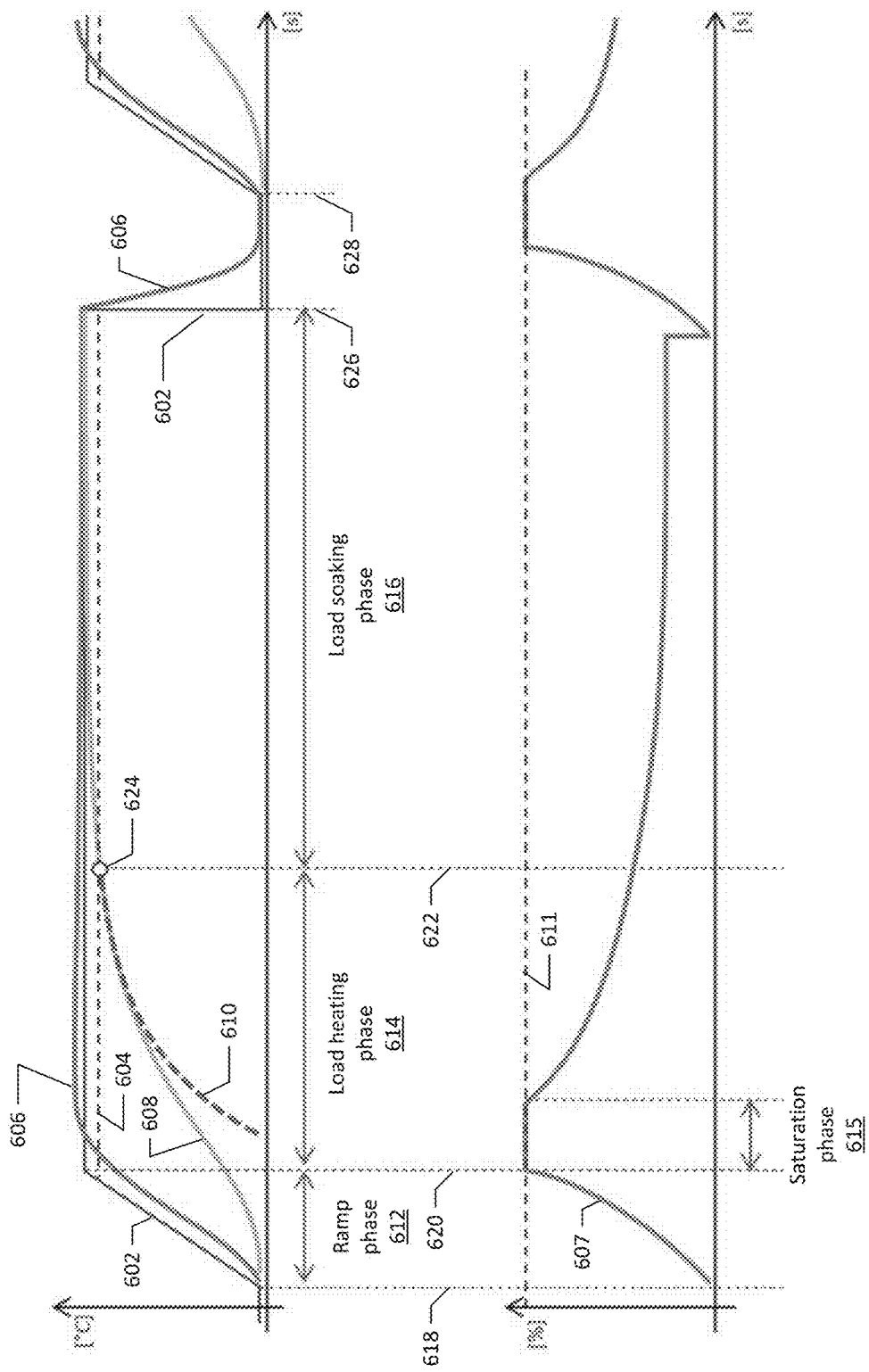
FIG. 6 illustrates an exemplary timeline of events during the user workflow of FIG. 5.

FIG. 6 illustrates an exemplary timeline of events during the steady-state execution phase of the user workflow. The timeline illustrates how controller 104 performs sensor-less identification of the end of the load heating phase. In an embodiment, during the steady-state execution phase, controller 104 performs a model-based strategy that adapts to different loads automatically to estimate the end of the load heating phase and advance to the next stage of the batch program as soon as possible to save time and energy.

The timeline of FIG. 6 includes a setpoint (SP) profile 602, a difference between a setpoint and a load threshold 604 (e.g., $SP-SS_{thr}$), a process variable (PV) (e.g., furnace temperature) profile 606, a load temperature (TL) profile 608, an estimated load temperature ($TL_{est}$) profile 610, a controller output (OP) profile 607, and a controller output maximum value 611 over a ramp phase 612, a load heating phase 614, a load soaking phase 616, and a saturation phase 615.

At time 618, load 120 enters furnace 106 and controller 104 begins the batch program. The steady-state function block component 110 monitors the furnace heating phase (e.g., ramp phase 612). The load temperature (TL) increases during ramp phase 612.

At time 620, the setpoint (e.g., setpoint profile 602) becomes constant and the steady-state function block component 110 begins a load temperature estimation procedure. At time 622, the steady-state function block component 110 estimates the steady-state condition of the load temperature (e.g., load temperature profile 608 and estimated load temperature profile 610) and the end of the load heating phase. In an embodiment, steady-state function block component 110 estimates the steady-state condition of the load temperature when the estimated load temperature ($TL_{est}$) 610 reaches the difference between the setpoint and the load threshold 604 (e.g., $SP-SS_{thr}$), as shown at point 624. The steady-state function block component 110 communicates the end of load heating phase 614 to setpoint programmer component 112, which begins load soaking phase 616. At time 626, the load soaking phase 616 ends and the load can be removed from the furnace. At time 628, a new batch begins and the process repeats.

Figure 7:
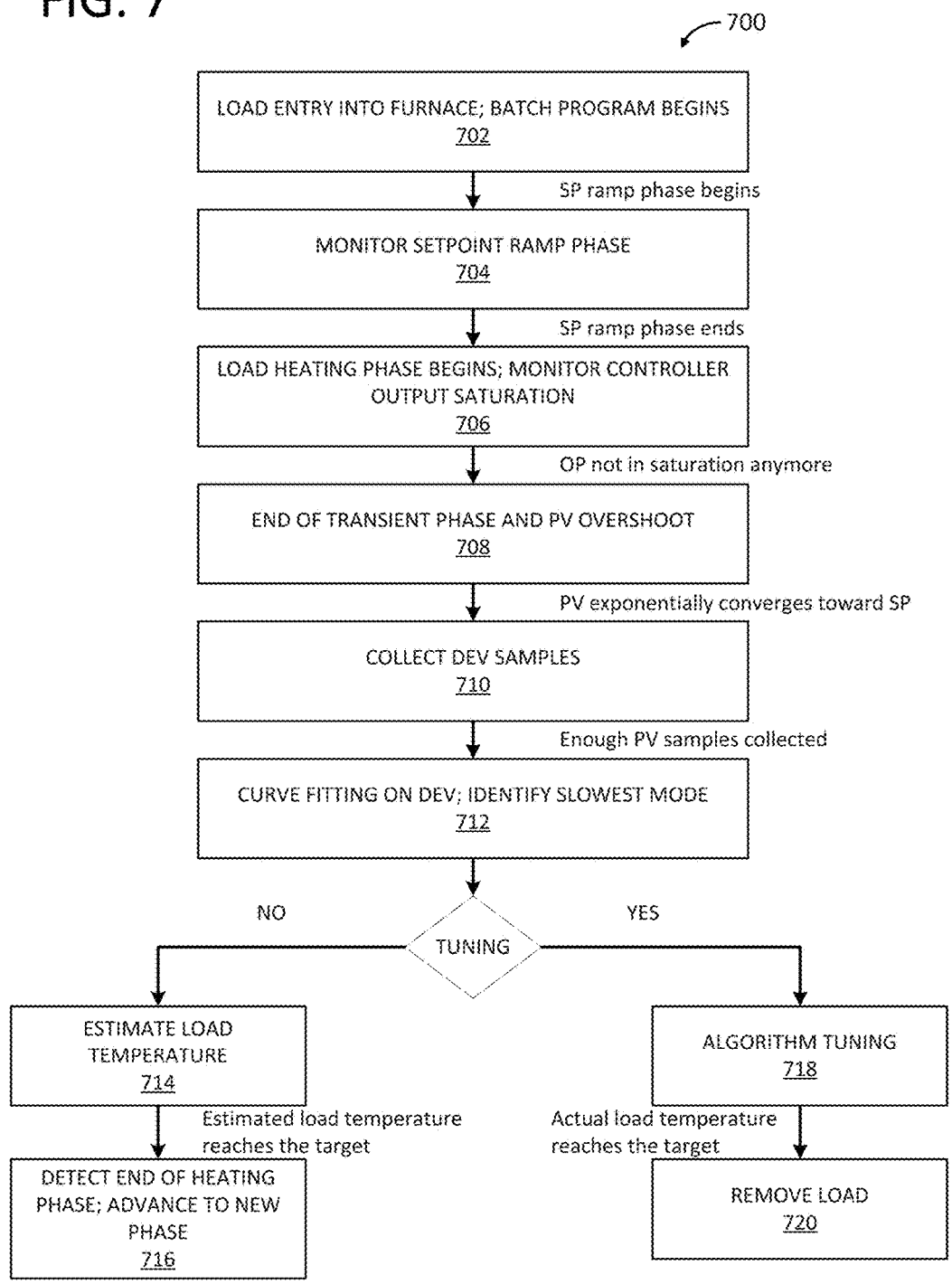
FIG. 7 illustrates an exemplary batch execution and steady-state tuning process according to an embodiment.

FIG. 7 illustrates an exemplary batch execution and steady-state tuning process 700. At step 702, load 120 is placed in furnace 106 and a user begins the batch program. In an embodiment, the transition from step 702 to step 704 coincides with the beginning of the setpoint ramp phase 612. At step 704, setpoint programmer component 112 communicates the ramp to steady-state function block component 110, which monitors the duration of the setpoint ramp phase 612. In an embodiment in which there is no ramp in the batch program, step 704 is skipped. At step 706, load heating phase 614 begins. In an embodiment in which the controller output (OP) is in saturation, the steady-state function block component 110 monitors the duration of controller output saturation phase 615. In an embodiment in which the controller output (OP) does not reach saturation, step 706 is skipped.

When the controller output (OP) is no longer in saturation, the steady-state algorithm waits for the beginning of the exponential decay of the controlled furnace temperature (PV) towards the setpoint (SP), at step 708. The algorithm waits for the occurrence of the PV overshoot as a condition of the beginning of the exponential decay. When the controlled furnace temperature (PV) is exponentially decaying toward the setpoint, controller 104 collects DEV=PV−SP samples at step 710. The DEV samples are collected by averaging the DEV value over a time period that is proportional (e.g., $1 \cdot T_i$) to the integral time constant of the PID loop component 114 (e.g., one of the tuning constants calculated during the PID loop auto-tuning). The base sampling and averaging period is defined as a multiple of $T_i$ that is the PID loop integral time constant (e.g., obtained with the auto-tuning process with an empty furnace). In an embodiment, the sampling time is doubled after a predetermined number (e.g., ten) of DEV samples. In an embodiment, the samples ($t_i$, $DEV_i$) are collected by averaging the DEV over the sampling period, as described in Equation (6).

$$DEV_i = \int_{t_i-\Delta t_s/2}^{t_i+\Delta t_s/2} DEV(t)dt \bigg/ \int_{t_i-\Delta t_s/2}^{t_i+\Delta t_s/2} tdt \qquad (6)$$

where t is the time, $t_i$ the median time of a sampling period and $\Delta t_s$ the current duration of the sampling period. The computational advantage of using DEV in place of PV with the sampling technique described by Equation (6) derives from the fact that DEV is calculated from PV by subtracting the constant offset SP.

When enough DEV samples have been collected, the samples are fit with a first-order exponential curve $DEV_{fit}=\delta \exp(-t/\tau)$ at step 712. Least square exponential curve fitting techniques are used to identify the exponential parameters ($\delta$, $\tau$) of the curve (i.e., the exponential parameters are identified by minimizing a cost function that depends on the sum of the squares of the offsets of the DEV samples ($t_i$, $DEV_i$) from the fitting curve $DEV_{fit}$). An exemplary cost function that may be minimized to identify the parameters ($\delta$, $\tau$) is reported in Equation (7a).

$$\sum_{i=1}^{N} DEV_i \cdot (\ln DEV_i - \ln \delta + t_i/\tau)^2 \qquad (7a)$$

From the minimization of the cost function in Equation (7a) the following exemplary best-fitting parameters ($\delta$, $\tau$) may be derived:

$$\delta = \exp\left( \frac{\sum_{i=1}^{N} t_i^2 DEV_i \cdot \sum_{i=1}^{N} DEV_i \ln DEV_i - \sum_{i=1}^{N} t_i DEV_i \cdot \sum_{i=1}^{N} t_i DEV_i \ln DEV_i}{\sum_{i=1}^{N} DEV_i \cdot \sum_{i=1}^{N} t_i^2 DEV_i - \left(\sum_{i=1}^{N} t_i DEV_i\right)^2} \right) \qquad (7b)$$

$$\tau = - \frac{\sum_{i=1}^{N} DEV_i \cdot \sum_{i=1}^{N} t_i^2 DEV_i - \left(\sum_{i=1}^{N} t_i DEV_i\right)^2}{\sum_{i=1}^{N} DEV_i \cdot \sum_{i=1}^{N} t_i DEV_i \ln DEV_i - \sum_{i=1}^{N} t_i DEV_i \cdot \sum_{i=1}^{N} DEV_i \ln DEV_i} \qquad (7c)$$

where ($t_i$, $DEV_i$) are the DEV samples and N is the number of DEV samples. In particular, $\tau$ is the time constant of the slowest decay mode of the system that is present in DEV, PV, OP, and TL. In an embodiment, a minimal set of samples (e.g., five) is required before the PV samples are fit, and consequently the load temperature is estimated. In an embodiment, when a maximum set of samples (e.g., ten) has been collected and a new sample has been calculated, the moving sampling set advances over time by discarding the oldest sample and by adding the last new sample to the set.

The exponential fit is performed on the moving sampling set until the steady-state mode is identified, which allows for adapting the fitted curve to the slowest decay mode shape present in DEV, PV, OP and TL.

When the algorithm is executed in the normal mode (i.e., no tuning), the controller 104 starts estimating the load temperature at step 714. At step 714, the PV fitted curve is mapped into the estimated load temperature by mapping DEV to TL. The scaling factors of the mapping equation are calculated from the identified exponential $DEV_{fit}$ curve and from the tuning parameter $TL_{tun}$. When the estimated load temperature reaches the target value (e.g., $SP-SS_{thr}$) then the steady-state function block component 110 communicates to the setpoint programmer component 112, at step 716, that the load heating phase has finished. The batch then advances to the next phase (e.g., load soaking phase 616).

When the algorithm is executed in the tuning mode (step 718), the load temperature (TL) is measured and known. When the load temperature reaches the target value (e.g., $SP-SS_{thr}$) the tuning parameter $TL_{tun}$ is calculated. The tuning parameter $TL_{tun}$ is used to calculate the scale factors of the mapping equation from the DEV fitted curve to the estimated TL and its value is such that the estimated load temperature reaches the target value (e.g., $SP-SS_{thr}$) at the same time as the actual load temperature. When the tuning procedure is completed, the load equipped with a temperature sensor (e.g., load 402 with load temperature sensor 404) is removed from furnace 106. After this tuning procedure, the batch programs can be executed with loads not equipped with a temperature sensor (e.g., load 120) by executing the steady-state function block component 110 in the normal mode, as described above.

Figure 8:
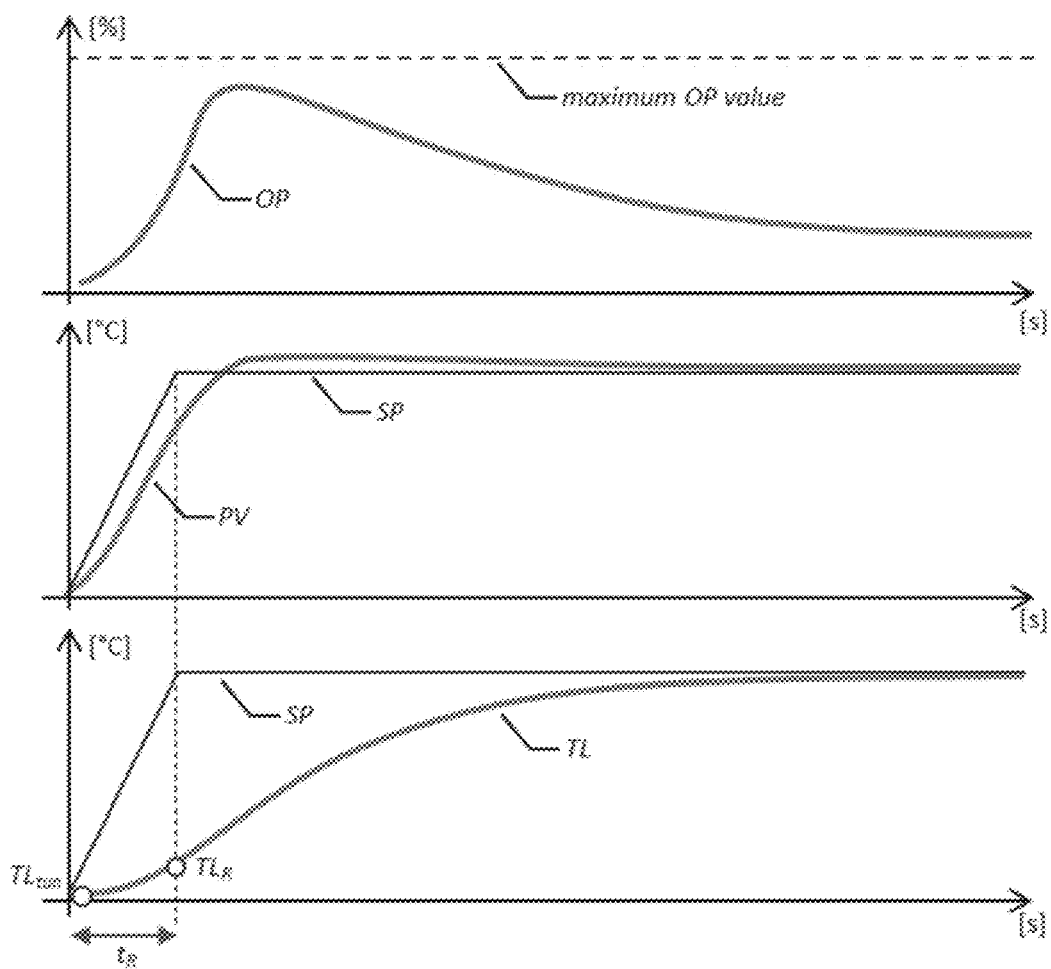
FIG. 8 illustrates exemplary value profiles of the control system of FIG. 1 during a ramp compensation time period according to an embodiment.

FIG. 8 illustrates values of system 100 during an exemplary ramp compensation time period. In an embodiment, controller 104 executing the algorithm assumes that the load temperature increases during the SP ramp phase by following the response to a ramp from $TL_{tun}$ to SP of a first-order linear dynamical system with a time constant proportional (e.g., 2·$\tau$) to the identified slowest mode:

$$TL_R = (SP - TL_{tun})\left(1 - \frac{k_R \tau}{t_R} \cdot \left(1 - e^{\frac{-t_R}{k_R \tau}}\right)\right) + TL_{tun} \qquad (8)$$

where $\tau$ is the slowest identified mode, $t_R$ is the ramp period, and $k_R$ is the multiplicative constant of $\tau$.

Figure 9:
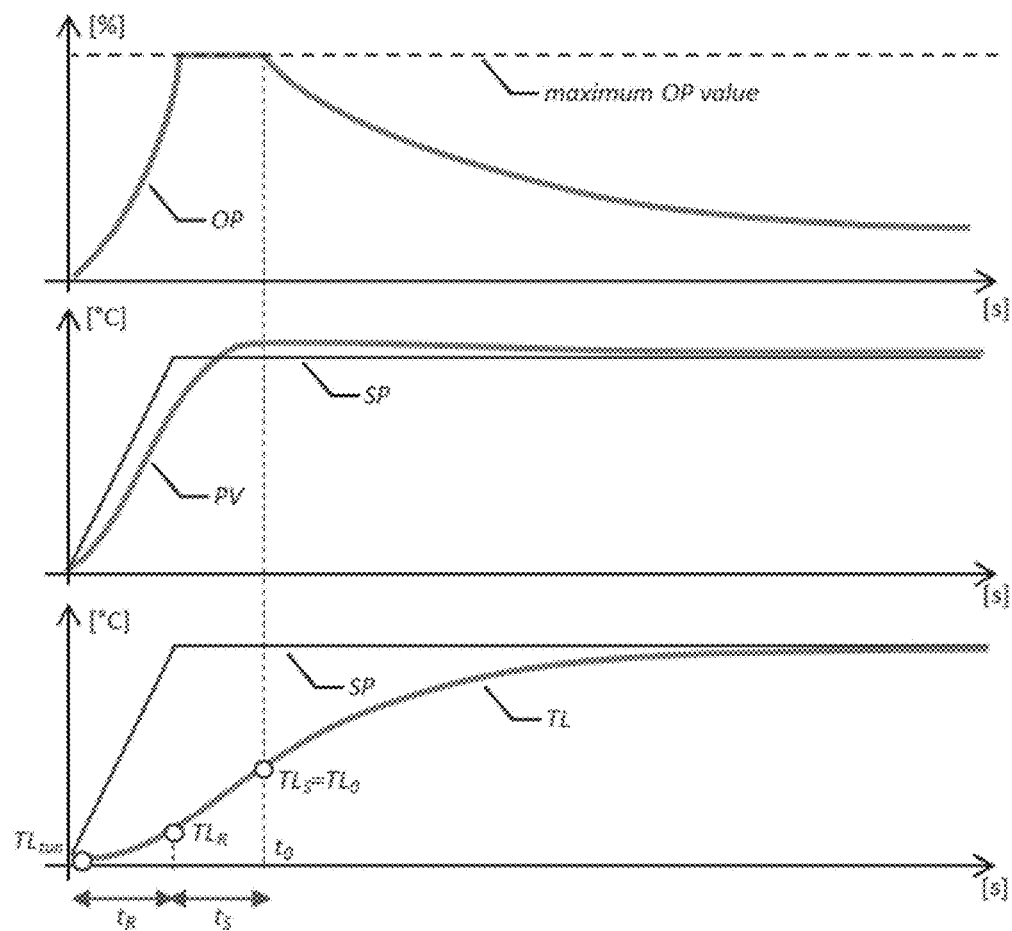
FIG. 9 illustrates exemplary value profiles of the control system of FIG. 1 during a saturation compensation time period according to an embodiment.

FIG. 9 illustrates values of system 100 during an exemplary saturation compensation time period. If the ramping period (which may be zero in one or more embodiments) is followed by a phase during which the OP is saturated, then the same method is used to calculate the increase of the load temperature. In an embodiment, extended saturation periods occur when a huge load is treated and an equilibrium is established between the full power supplied by the heaters and the heat absorbed by the load, by leading to ramping PV and TL profiles. In an embodiment, controller 104 executing the algorithm assumes that the load temperature increases further during the OP saturation phase by following the response of ramp from $TL_R$ to SP of a first-order linear dynamical system with a time constant proportional (e.g., 1·$\tau$) to the identified slowest mode:

$$TL_S = (SP - TL_R)\left(1 - \frac{k_S \tau}{t_S} \cdot \left(1 - e^{\frac{-t_S}{k_S \tau}}\right)\right) + TL_R \qquad (9)$$

where τ is the slowest identified mode, $t_S$ is the saturation period, and $k_S$ is the multiplicative constant of τ.

Figure 10:
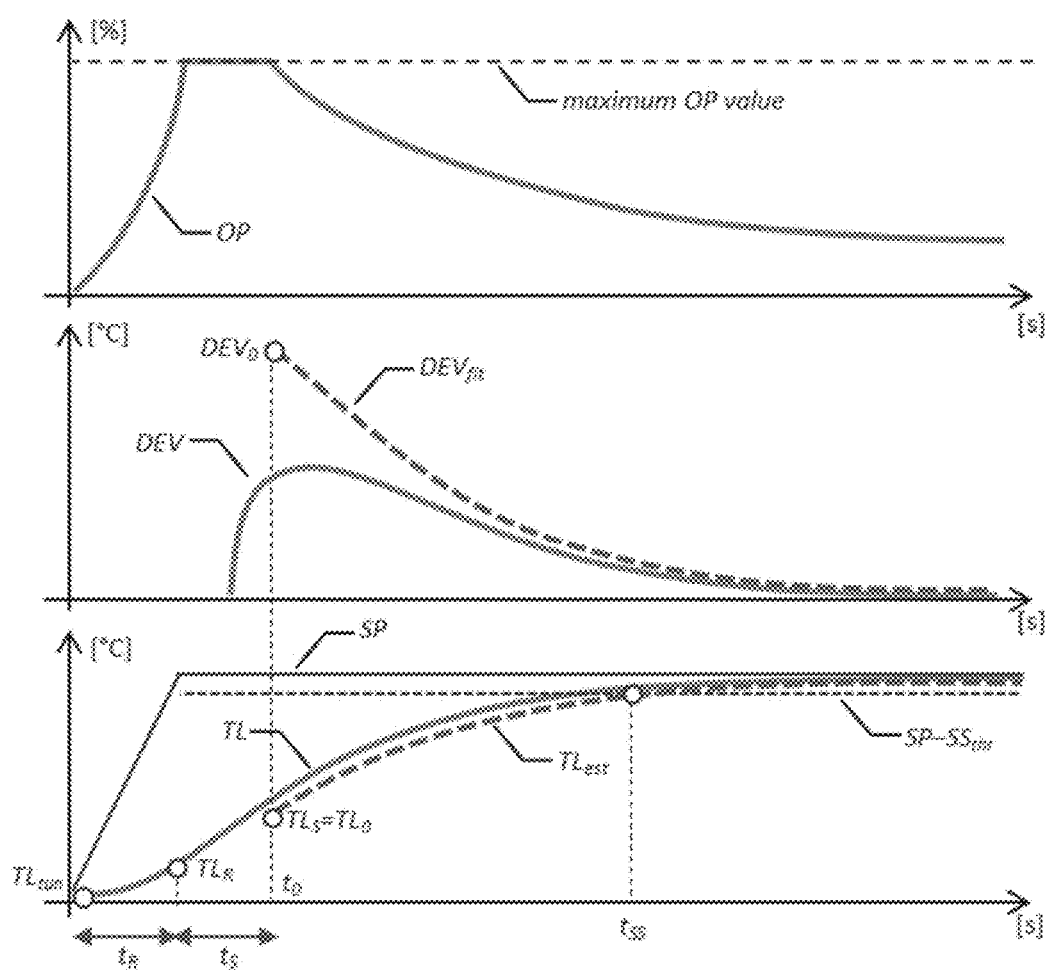
FIG. 10 illustrates exemplary value profiles of the control system of FIG. 1 during an auto-tune procedure according to an embodiment.

FIG. 10 illustrates values of system 100 during an exemplary auto-tune with compensation for SP ramp and OP saturation. The auto-tune final equation compensates for the ramp and saturation effect on $TL_0$ by using the previous equations of $TL_R$ and $TL_S$:

$$TL_0 = TL_S(TL_R(TL_{tun})) = TL_0(SP, \tau, t_R, t_S, TL_{tun}) \quad (10)$$

By solving for $TL_{tun}$ the expression used in the auto-tune procedure is:

$$TL_{tun} = \frac{TL_0 - (\gamma_R + \gamma_S - \gamma_S \gamma_R)SP}{1 - (\gamma_R + \gamma_S - \gamma_S \gamma_R)} \quad (11)$$

where $$\gamma_R = 1 - \frac{\tau}{t_R} \cdot \left(1 - e^{\frac{-t_R}{k_R \tau}}\right), \gamma_S = 1 - \frac{\tau}{t_S} \cdot \left(1 - e^{\frac{-t_S}{k_S \tau}}\right) \quad (12)$$

During normal execution of the algorithm the value of $TL_0$ is adjusted to account for the setpoint being different from the setpoint fit ($SP_{fit}$) used during the auto-tune sequence:

$$TL_0 = TL_0\left(SP, \tau, t_R, t_S, TL_{tun} \cdot \frac{SP}{SP_{fit}}\right) \quad (13)$$

Figure 11:
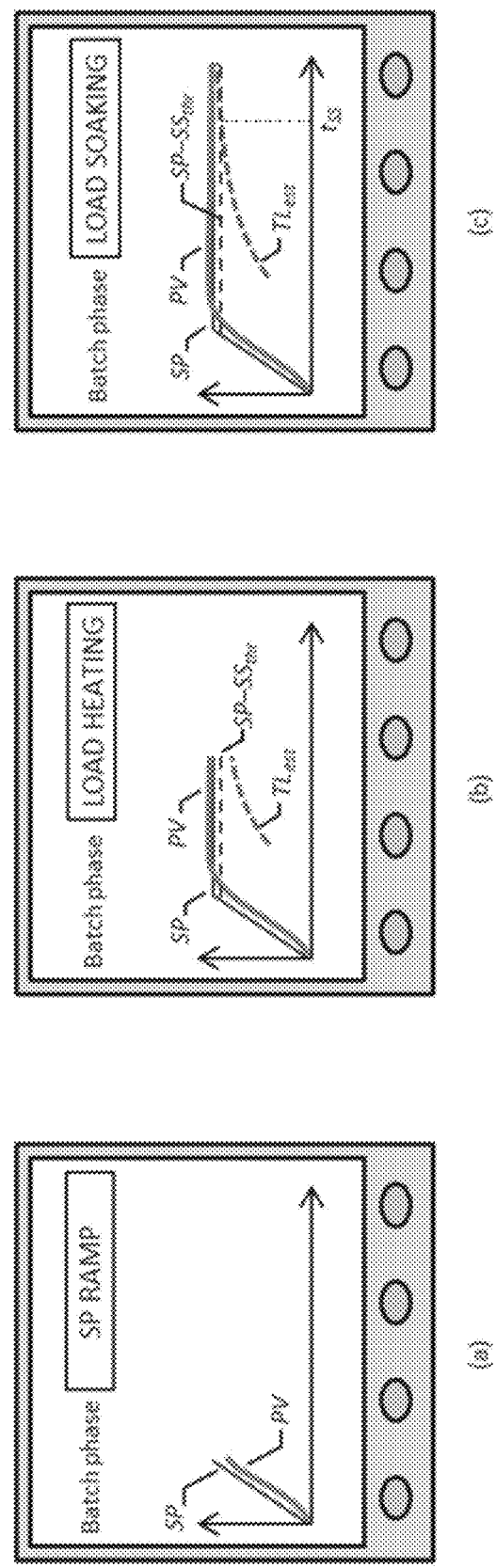
FIG. 11 illustrates exemplary human machine interface device screens according to an embodiment.

FIG. 11 illustrates exemplary human-machine interface (HMI) 102 visualization screens displayed to the user during the execution of the sensor-less identification of the load steady-state condition. After the user has configured the batch program (e.g., user sets load temperature threshold $SS_{thr}$, temperature setpoint SP value, SP ramp rate, load soaking phase duration), the load 120 is entered in the furnace 106. After inserting the load 120, the user starts the batch program, which causes the SP ramp phase to start. The HMI device 102 displays the current status of the batch (e.g., "SP RAMP") and the temperature setpoint SP and process variable profiles (e.g., profiles 602 and 606, respectively) over time ramping towards the SP target value (see FIG. 8(a)). When the SP has reached its target value the batch phase advances and the HMI device 102 displays the new status (e.g., "LOAD HEATING"). When the controller 104 starts the load temperature estimation, the HMI device 102 displays the estimated load temperature profile $TL_{est}$ over time converging to the target SP. When the estimated load temperature reaches the difference between the temperature setpoint and the user-entered threshold (e.g., $TL_{est} = SP - SS_{thr}$), then controller 104 communicates to the HMI device 102 the end of the load heating phase and the start of the next phase of the batch, and the HMI device 102 displays the new status (e.g., "LOAD SOAKING").

In an aspect, a system includes a heat treatment furnace, a controller, and a human machine interface coupled to the controller. The controller is coupled to the furnace for controlling one or more operating parameters of the furnace (e.g., a process variable PV is an atmosphere temperature within the furnace, and it is controlled to reach the user-entered setpoint SP) and performing a batch program composed by different phases including a load heating phase, that finishes when the load reaches steady-state condition. In an embodiment, the controller receives from the human machine interface the parameters and settings which define the heat-treatment, such as a setpoint temperature SP and a load temperature threshold $SS_{thr}$ that defines the steady-state load condition (e.g., $TL = SP - SS_{thr}$). The controller includes a computer-readable storage device storing processor-executable instructions that, when executed, generate in real-time an estimate of a temperature TL of a load within the heat treatment furnace and automatically advances from the load heating phase to the next batch phase when it estimates that TL has the steady-state condition. The controller collects, during the load heating phase, samples of an available control loop signal when it is exponentially converging toward its steady-state value (e.g., a process variable PV is exponentially decaying toward a temperature setpoint SP, or a process deviation DEV=PV−SP that is exponentially decaying toward zero, or a controller output OP that is exponentially decaying toward a steady-state value). The controller fits the collected samples with an exponential curve representing the slowest decay mode of the control loop signal. The same slowest mode characterized by the same time constant is present in all the control loop signals and it is due to the load dynamics. The controller generates a load temperature $TL_{est}$ estimate by mapping the fitted exponential curve to $TL_{est}$. The controller advances to the next phase of the batch program when the estimated temperature reaches the difference between a temperature setpoint SP and a user defined load threshold $SS_{thr}$ (e.g., $TL_{est} = SP - SS_{thr}$). In an embodiment, the controller communicates the real-time load temperature estimation $TL_{est}$ to the human machine interface, which displays $TL_{est}$ to the user. In another embodiment, the controller communicates the estimated end of the load heating phase (e.g., when $TL_{est} = SP - SS_{thr}$) to the human machine interface, which displays the change of the phase of the batch program to the user.

In another aspect, a controller executing computer-executable instructions monitors a setpoint ramp phase and a controller output saturation phase, during which heat is applied to a load within a heat treatment furnace. The controller collects samples of a control loop signal of the controller when the control loop signal is exponentially converging toward its steady-state value (e.g., a process variable PV is exponentially converging toward a temperature setpoint, or a process deviation DEV=PV−SP is exponentially converging toward zero, or a controller output OP that is exponentially decaying toward a steady-state value). The controller fits the collected samples with an exponential curve that is characterized by the time constant of the slowest exponential mode that is present in all the control loop signals. The controller maps the fitted curve to estimate $TL_{est}$ the temperature of the load TL by adjusting the scale factors of the mapping equation depending on the duration of the setpoint ramp phase and controller output saturation phase. And the controller automatically advances to the next batch phase when it establishes that the load has reached steady-state temperature by assessing whether the estimated load temperature reached the difference between the temperature setpoint SP and a user-entered load threshold $SS_{thr}$ (e.g., $TL_{est} = SP - SS_{thr}$).

In yet another aspect, a tuning procedure is embodied for the sensor-less load temperature estimation. A PID loop component of a controller is tuned against a heat treatment furnace in the absence of a load to generate a tuning set. The controller stores the tuning set in a computer-readable storage device. A load whose dynamics is dominant against the other system components, which includes a temperature sensor, is inserted into the heat treatment furnace. The controller receives a load threshold value of the temperature of the load from a setpoint temperature value and measures the temperature of the load while a heat source of the furnace is applied to the load. The controller collects samples of a control loop signal when the control loop signal is exponentially converging toward its steady-state value with a sampling frequency that depends on the PID loop tuning set. The controller fits the collected samples with an exponential curve. The controller establishes the values of the mapping parameters from the sampled control loop signal and the estimated load temperature, by calculating the parameters that make the load estimated temperature and the actual load temperature coincide. The load is removed from the furnace and a sensor-less production load is inserted into the furnace. The controller estimates the temperature of the production load while the heat source of the furnace is applied to it based on the stored mapping parameters.

In addition to the embodiment described above with respect to FIG. 1, embodiments of the present disclosure may comprise a special purpose computer including a variety of computer hardware, as described in greater detail below.

Embodiments within the scope of the present disclosure also include computer-readable media for carrying or having computer-executable instructions or data structures stored thereon. Such computer-readable media can be any available media that can be accessed by a special purpose computer. By way of example, and not limitation, computer-readable storage media include both volatile and nonvolatile, removable and non-removable media implemented in any method or technology for storage of information such as computer readable instructions, data structures, program modules or other data. Computer storage media are non-transitory and include, but are not limited to, random access memory (RAM), read only memory (ROM), electrically erasable programmable ROM (EEPROM), compact disk ROM (CD-ROM), digital versatile disks (DVD), or other optical disk storage, solid state drives (SSDs), magnetic cassettes, magnetic tape, magnetic disk storage, or other magnetic storage devices, or any other medium that can be used to carry or store desired program code means in the form of computer-executable instructions or data structures and that can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which aspects of the disclosure may be implemented. Although not required, aspects of the disclosure will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that aspects of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Aspects of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing aspects of the disclosure includes a special purpose computing device in the form of a conventional computer, including a processing unit, a system memory, and a system bus that couples various system components including the system memory to the processing unit. The system bus may be any of several types of bus structures including a memory bus or memory controller, a peripheral bus, and a local bus using any of a variety of bus architectures. The system memory includes nonvolatile and volatile memory types. A basic input/output system (BIOS), containing the basic routines that help transfer information between elements within the computer, such as during start-up, may be stored in ROM. Further, the computer may include any device (e.g., computer, laptop, tablet, PDA, cell phone, mobile phone, a smart television, and the like) that is capable of receiving or transmitting an IP address wirelessly to or from the internet.

The computer may also include a magnetic hard disk drive for reading from and writing to a magnetic hard disk, a magnetic disk drive for reading from or writing to a removable magnetic disk, and an optical disk drive for reading from or writing to removable optical disk such as a CD-ROM or other optical media. The magnetic hard disk drive, magnetic disk drive, and optical disk drive are connected to the system bus by a hard disk drive interface, a magnetic disk drive-interface, and an optical drive interface, respectively. The drives and their associated computer-readable media provide nonvolatile storage of computer-executable instructions, data structures, program modules, and other data for the computer. Although the exemplary environment described herein employs a magnetic hard disk, a removable magnetic disk, and a removable optical disk, other types of computer readable media for storing data can be used, including magnetic cassettes, flash memory cards, digital video disks, Bernoulli cartridges, RAMs, ROMs, SSDs, and the like.

Communication media typically embody computer readable instructions, data structures, program modules or other data in a modulated data signal such as a carrier wave or other transport mechanism and includes any information delivery media.

One or more aspects of the disclosure may be embodied in computer-executable instructions (i.e., software), routines, or functions stored in system memory or nonvolatile memory as application programs, program modules, and/or program data. The software may alternatively be stored remotely, such as on a remote computer with remote application programs. Generally, program modules include routines, programs, objects, components, data structures, etc. that perform particular tasks or implement particular abstract data types when executed by a processor in a computer or other device. The computer executable instructions may be stored on one or more tangible, non-transitory computer readable media (e.g., hard disk, optical disk, removable storage media, solid state memory, RAM, etc.) and executed by one or more processors or other devices. As will be appreciated by one of skill in the art, the functionality of the program modules may be combined or distributed as desired in various embodiments. In addition, the functionality may be embodied in whole or in part in firmware or hardware equivalents such as integrated circuits, application specific integrated circuits, field programmable gate arrays (FPGA), and the like.

The computer may operate in a networked environment using logical connections to one or more remote computers. The remote computers may each be another personal computer, a tablet, a PDA, a server, a router, a network PC, a peer device, or other common network node, and typically include many or all of the elements described above relative to the computer. The logical connections include a local area network (LAN) and a wide area network (WAN) that are presented here by way of example and not limitation. Such networking environments are commonplace in office-wide or enterprise-wide computer networks, intranets and the Internet.

When used in a LAN networking environment, the computer is connected to the local network through a network interface or adapter. When used in a WAN networking environment, the computer may include a modem, a wireless link, or other means for establishing communications over the wide area network, such as the Internet. The modem, which may be internal or external, is connected to the system bus via the serial port interface. In a networked environment, program modules depicted relative to the computer, or portions thereof, may be stored in the remote memory storage device. It will be appreciated that the network connections shown are exemplary and other means of establishing communications over wide area network may be used.

Preferably, computer-executable instructions are stored in a memory, such as the hard disk drive, and executed by the computer. Advantageously, the computer processor has the capability to perform all operations (e.g., execute computer-executable instructions) in real-time.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the disclosure.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A system comprising:
   a heat treatment furnace;
   a controller coupled to the furnace for controlling one or more operating parameters thereof; and
   a human machine interface coupled to the controller;
   wherein the controller includes a computer-readable storage device storing processor-executable instructions that, when executed, generate in real-time an estimate of a temperature of a load within the heat treatment furnace and perform a batch program, said batch program comprising a load heating phase and at least one other phase, the processor-executable instructions comprising:
   receiving a temperature setpoint and a load threshold via the human machine interface;
   collecting samples of a control loop signal when said signal is exponentially converging toward the steady-state value;
   fitting the collected samples with an exponential curve representing the slowest decay mode of the control loop signal;
   generating the estimate of the temperature of the load by mapping the fitted exponential curve to the estimate of the temperature of the load; and
   advancing the batch program from the load heating phase to the at least one other phase when the estimate of the temperature of the load reaches the difference between the temperature setpoint and the load threshold.

2. The system of claim 1, wherein the controller adjusts at least one of the one or more operating parameters based on the estimate of the temperature of the load.

3. The system of claim 1, the processor-executable instructions further comprising monitoring the duration of a setpoint ramp phase.

4. The system of claim 1, wherein the samples are collected on a moving time window, and wherein each collected sample is the mean of the real-time values acquired during the sampling period.

5. The system of claim 4, the processor-executable instructions further comprising iteratively identifying the exponential curve by applying a least square error method to the collected samples during the moving time window.

6. The system of claim 1, wherein the controller receives the temperature setpoint via the human-machine interface.

7. The system of claim 1, the processor-executable instructions further comprising detecting a steady-state temperature of the load when the estimate of the temperature of the load is within a user-defined threshold value from the temperature setpoint.

8. A method comprising:
   monitoring, by a controller executing computer-executable instructions therefor, a setpoint ramp phase and a controller output saturation phase of a batch, wherein heat is applied to a load within a heat treatment furnace during the setpoint ramp phase and the controller output saturation phase;

collecting, by the controller executing computer-executable instructions therefor, samples of a control loop signal of the controller when the control loop signal is exponentially converging toward a steady-state value thereof;

fitting, by the controller executing computer-executable instructions therefor, the collected samples with an exponential curve characterized by a time constant of a slowest exponential mode present in the control loop signal;

mapping, by the controller executing computer-executable instructions therefor, the fitted curve to estimate the temperature of the load; and advancing, by the controller executing computer-executable instructions therefor, the batch to another phase when the estimated temperature of the load reaches the difference between a temperature setpoint and a load threshold.

9. The method of claim 8, further comprising adjusting, by the controller executing computer-executable instructions therefor, at least one of one or more operating parameters of the heat treatment furnace based on the estimate of the temperature of the load.

10. The method of claim 8, wherein said collecting samples comprises collecting samples on a moving time window, wherein each collected sample is the mean of the real-time values acquired during a sampling period.

11. The method of claim 10, further comprising iteratively identifying, by the controller executing computer-executable instructions therefor, the exponential curve by applying a least square error method to the collected samples during the moving time window.

12. The method of claim 8, further comprising receiving, by the controller executing computer-executable instructions therefor, the temperature setpoint from a user human-machine interface device coupled to the controller.

13. The method of claim 8, further comprising detecting, by the controller executing computer-executable instructions therefor, a steady-state temperature of the load when the estimate of the temperature of the load is within a user-defined threshold value from the temperature setpoint.

14. A method of tuning a controller for sensor-less load temperature estimation, comprising:

tuning a PID loop component of a controller against a heat treatment furnace in the absence of a load therein to generate a tuning set;

storing, by the controller, the tuning set in a computer-readable storage device of the controller, wherein the controller is coupled to the heat treatment furnace;

inserting a load into the heat treatment furnace, the load including a temperature sensor therein, and the load having dominant dynamics;

receiving, by the controller, a target threshold value of the temperature of the load from a setpoint temperature value;

measuring, by the controller, the temperature of the load while a heat source of the heat treatment furnace is applied thereto;

sampling, by the controller, a control loop signal when said signal is exponentially converging toward a steady-state value thereof;

fitting, by the controller, the samples with an exponential curve;

establishing, by the controller, values of mapping parameters from the sampled control loop signal and an estimate of the temperature of the load;

removing the load from the heat treatment furnace;

inserting a sensor-less production load into the heat treatment furnace; and estimating, by the controller, the temperature of the production load while the heat source of the heat treatment furnace is applied thereto based on the established values of the mapping parameters.

15. The method of claim 14, further comprising receiving, by the controller, the setpoint load temperature value from a user human-machine interface device coupled to the controller.

16. The method of claim 14, wherein said estimating the temperature of the production load comprises:

collecting, by the controller, samples of an output signal of the controller when an atmospheric temperature within the heat treatment furnace is exponentially decaying toward the setpoint load temperature value;

fitting, by the controller, the collected samples with an exponential curve representing the exponential decay of the atmospheric temperature within the heat treatment furnace; and mapping, by the controller, the fitted curve to generate the estimate of the temperature of the load.

17. The method of claim 16, further comprising adjusting, by the controller, one or more operating parameters of the heat treatment furnace based on the estimate of the temperature of the load.

18. The method of claim 16, wherein said collecting samples comprises collecting samples on a moving time window, wherein each collected sample is the mean of the real-time values acquired during a sampling period.

19. The method of claim 18, further comprising iteratively identifying, by the controller, the exponential curve by applying a least square error method to the collected samples during the moving time window.

20. The method of claim 16, further comprising detecting, by the controller, a steady-state temperature of the load when the estimate of the temperature of the load is within a user-defined threshold value from the temperature setpoint.

* * * * *